(12) United States Patent
Gellman (10) Patent No.: US 7,029,450 B2
(45) Date of Patent: Apr. 18, 2006

(54) DILATION CATHETER ASSEMBLY AND RELATED METHODS

(75) Inventor: Barry N. Gellman, N. Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 490 days.

(21) Appl. No.: 10/020,345

(22) Filed: Dec. 14, 2001

(65) Prior Publication Data

US 2003/0114877 A1 Jun. 19, 2003

(51) Int. Cl.
*A61B 5/00* (2006.01)
(52) U.S. Cl. ........................... 600/549; 606/170
(58) Field of Classification Search ............... 606/192, 606/32–35, 27, 194, 159; 600/549
See application file for complete search history.

(56) References Cited

U.S. PATENT DOCUMENTS

| 3,661,142 | A | 5/1972 | Flam .................... 128/2 H |
| 3,830,224 | A | 8/1974 | Vanetti et al. ........... 128/2 H |
| 3,998,210 | A | 12/1976 | Nosari .................. 128/2 H |
| 4,015,591 | A | 4/1977 | Suzuki et al. ........... 128/2 R |
| 4,064,872 | A | 12/1977 | Caplan .................. 128/2 H |
| 4,087,575 | A | 5/1978 | Bichara ................... 428/1 |
| 4,175,543 | A | 11/1979 | Suzuki et al. ............ 128/736 |
| 4,362,645 | A | 12/1982 | Hof et al. ............... 252/408.1 |
| 4,643,186 | A | 2/1987 | Rosen et al. ............ 128/303.1 |
| RE32,743 | E | 9/1988 | Meyers et al. ........... 128/736 |
| 4,878,492 | A | 11/1989 | Sinofsky et al. ......... 128/303.1 |
| 5,009,655 | A | 4/1991 | Daignault, Jr. et al. ....... 606/7 |
| 5,176,693 | A | 1/1993 | Pannek, Jr. ............. 606/159 |
| 5,196,024 | A | 3/1993 | Barath ................. 606/159 |
| 5,248,305 | A | 9/1993 | Zdrahala ............... 604/280 |
| 5,320,634 | A | 6/1994 | Vigil et al. ............. 606/159 |
| 5,413,557 | A | 5/1995 | Solar |
| 5,498,261 | A | 3/1996 | Strul |
| 5,554,163 | A | 9/1996 | Shturman |
| 5,628,746 | A | 5/1997 | Clayman ................. 606/45 |
| 5,649,941 | A | 7/1997 | Lary ................... 606/159 |
| 5,651,047 | A | 7/1997 | Moorman et al. ........... 378/988 |
| 5,742,019 | A | 4/1998 | Radisch, Jr. ............. 219/69.17 |
| 5,779,698 | A | 7/1998 | Clayman et al. ........... 606/39 |
| 5,797,935 | A | 8/1998 | Barath ................. 606/159 |

(Continued)

FOREIGN PATENT DOCUMENTS

GB 2 308 652 A 7/1997

(Continued)

OTHER PUBLICATIONS

International Search Report in PCT/US02/36321 dated Mar. 27, 2003.

(Continued)

*Primary Examiner*—(Jackie) Tan-Uyen T. Ho (57) ABSTRACT

The invention, in one embodiment, is directed to a catheter assembly adapted to enable an operator to incise a human ureter from within, with reduced risk of damaging a crossing blood vessel. The dilation catheter includes an elongated body and a dilatable bladder. The dilatable bladder is adapted to dilate in a radially outward direction from the elongated body. A thermally responsive indicator incorporated with at least a portion of the dilation member exhibits a state change in response to a change in temperature. A temperature change indicates the existence of a nearby crossing vessel. In a surgical method, an operator repeatedly positions and inflates the dilatable bladder in a human ureter proximal to a desired incision location to map the location of any crossing vessels. The operator then determines an inner wall incision location that avoids the detected crossing vessels.

41 Claims, 8 Drawing Sheets

U.S. PATENT DOCUMENTS

| | | | |
|---|---|---|---|
| 5,806,528 A | 9/1998 | Magliochetti | 128/897 |
| 5,846,247 A | 12/1998 | Unsworth et al. | |
| 5,879,306 A | 3/1999 | Fontenot et al. | 600/473 |
| 5,904,679 A | 5/1999 | Clayman | 606/39 |
| 5,910,816 A | 6/1999 | Fontenot et al. | 348/65 |
| 5,967,984 A | 10/1999 | Chu et al. | 600/439 |
| 6,066,113 A | 5/2000 | Overtoom | 604/96 |
| 6,117,150 A | 9/2000 | Pingleton et al. | 606/167 |
| 6,165,187 A | 12/2000 | Reger | 606/159 |
| 6,176,871 B1 | 1/2001 | Pathak et al. | 623/1 |
| 6,179,195 B1 | 1/2001 | Adams et al. | 227/180.1 |
| 6,179,776 B1 | 1/2001 | Adams et al. | 600/121 |
| 6,203,508 B1* | 3/2001 | Ren et al. | 600/587 |
| 6,245,135 B1 | 6/2001 | Jaeger et al. | 106/31.29 |
| 6,248,117 B1 | 6/2001 | Blatter | 606/153 |
| 6,254,601 B1 | 7/2001 | Burbank et al. | |
| 6,261,247 B1 | 7/2001 | Ishikawa et al. | 600/587 |
| 6,263,230 B1 | 7/2001 | Haynor et al. | 600/424 |
| 6,264,689 B1 | 7/2001 | Colgan et al. | 623/1.22 |
| 6,296,651 B1 | 10/2001 | Lary et al. | |
| 6,432,062 B1* | 8/2002 | Ren et al. | 600/549 |
| 6,450,971 B1* | 9/2002 | Andrus et al. | 600/549 |
| 6,712,771 B1 | 3/2004 | Haddock et al. | |
| 2001/0047138 A1 | 11/2001 | Kokate et al. | |

FOREIGN PATENT DOCUMENTS

| | | |
|---|---|---|
| WO | 01/34062 A2 | 5/2001 |

OTHER PUBLICATIONS

"Scantek Medical Receives Patent for Prostate Examination Device, ProstAlert-tm," May. 23, 2001, *Business Wire*, May 22, 2001.

Umekawa et al. "Endopyelotomy With Ureteral Cutting Balloon Device: Long Term Follow Up of 13 Patents," Department of Urology, Kinki University School of Medicine, Aug. 1999, vol. 90, No. 8.

Beckmann, MD et al. "Secondary Ureteropelvic Junction Stricture: Percutaneous Dilation," *Radiology*, Aug. 1987, vol. 164, No. 2, pp. 365-367.

Lechevallier, MD et al. "Retrograde Acucise® Endopyelotomy: Long-Term Results," *Journal of Endourology*, Oct. 1999, vol. 13, No. 8, pp. 575-578.

"Letters tro the Editor," *The Journal of Urology*, Feb. 2001, vol. 165, pp. 542-545.

Sosa, R. Ernest, "Editorial: Endopyelotomy—Should it Become First Line Treatment for Ureteropelvic Obstruction?," *The Journal of Urology*, Sep. 1998, vol. 160, No. 3, pp. 698-699.

Shalhav et al. "Adult Endopyelotomy: Impact of Etiology and Antegrade Versus Retrograde Approach on Outcome," *The Journal of Urology*, Sep. 1998, vol. 160, No. 3, pp. 685-689.

Gelet et al. "Endopyelotomy With the Acucise Cutting Balloon Device," *European Urology*, May 1997, vol. 31, pp. 389-393.

Preminger, et al. "A Multicenter Clinical Trial Investigating the Use of a Fluroscopically Controlled Cutting Balloon Catheter for the Management of Ureteral and Ureteropelvic Junction Obstruction," *The Journal of Urology*, May 1997, vol. 157, pp. 1625-1629.

Cassis et al. "Endopyelotomy: Review of Results and Complications," *Journal of Urology*, Dec. 1991, vol. 146, pp. 1492-1495.

Makada, MD. et al. "Comparision of Acucise Endopyelotomy and Endoballoon Rupture for Management of Secondary Proximal Ureteral Stricture in the Porcine Model," *Journal of Endourology*, Aug. 1996, vol. 10, No.4, pp. 311-318.

Kim et al. "Use of New Technology in Endourology and Laparoscopy by American Urologists: Internet and Postal Survey," *Urology*, Nov. 2000, vol. 55, No. 5, pp. 760-765.

Pattaras, MD et al. "Laparoscopic Pyeloplasty," *Journal of Endourology*, Dec. 2000, vol. 14, No. 10, pp. 895-904.

* cited by examiner

DILATION CATHETER ASSEMBLY AND RELATED METHODS

FIELD OF THE INVENTION

The invention relates generally to dilation catheters. More particularly, in one embodiment, the invention is directed to a dilation catheter assembly adapted for performing an endopylotomy.

BACKGROUND OF THE INVENTION

An endopylotomy is performed to expand the size of a lumen of a patient's ureter to enable, for example, passage of stones and/or stone fragments through the lumen. Constriction of the ureter lumen may be caused at the ureteropelvic junction (UPJ) from pressure created by crossing vessels, such as, the femoral artery and/or vein. Surgical intervention is often performed to relieve the ureteral pressure by cutting through the ureteral wall at a location opposite the crossing vessel(s) to relax the ureteral lumen. Once performed, a stent is placed within the lumen until ureteral healing occurs.

Figure 1A:
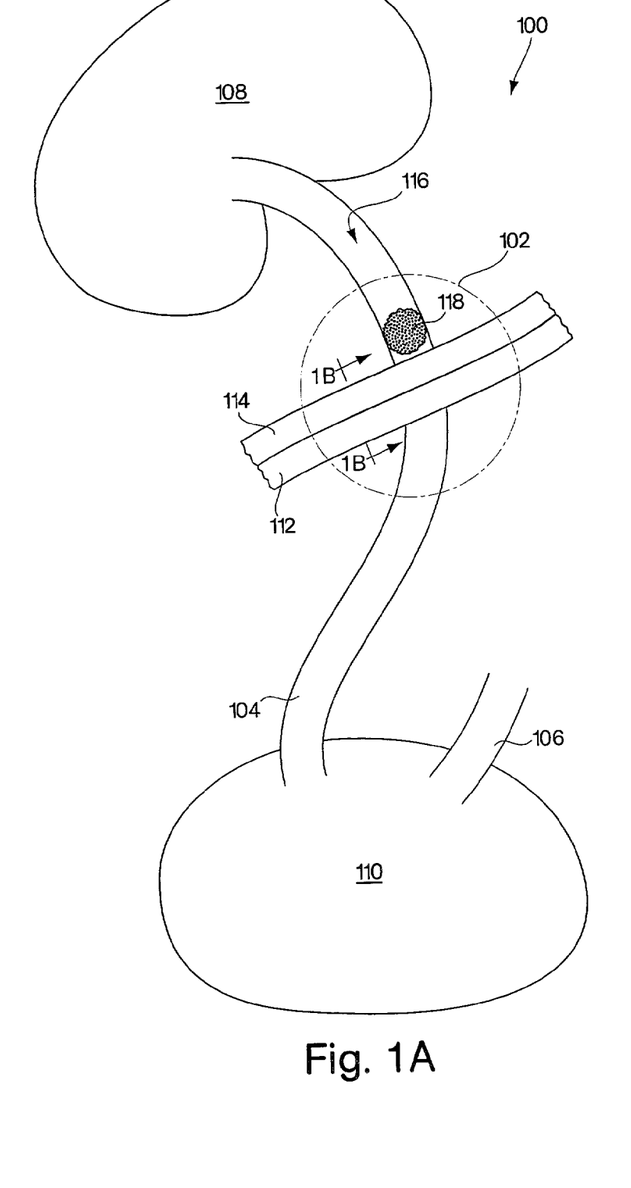
FIG. 1A is a schematic view of a portion of a human urinary tract including the ureteral pelvic junction (UPJ)
Figure 1B:
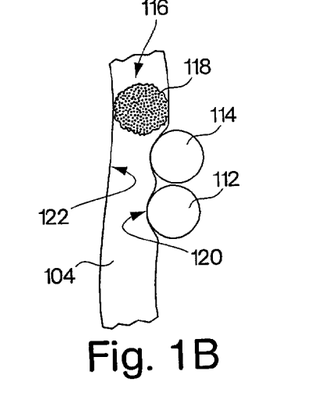
FIG. 1B is a cross-sectional view of the UPJ of FIG. 1A taken along line 1B—1B.

FIGS. 1A and 1B are conceptual background drawings showing a portion 100 of a human urinary tract being obstructed at the UPJ 102. Referring to FIGS. 1A and 1B, in a human urinary tract 100, the ureters 104 and 106 transport urine from the kidneys, one of which is shown at 108, to the bladder 110. The femoral artery 112 and femoral vein 114 cross the ureter 104 at the UPJ 102.

As shown in FIG. 1B, on occasion, the femoral artery 112 and/or the femoral vein 114 exert pressure on the ureter 104 and restrict urine flow through the ureter lumen 116. Under normal circumstances, this may not cause discomfort. However, such obstruction may inhibit passage of a stone or stone fragment, such as the stone 118, from the kidney 108 to the bladder 110. As describe above, an endopylotomy can be performed to reduce the restriction in the ureter lumen 116. However, such a procedure is not without risk. For example, if a medical operator cuts the ureter lumen 116 on the inside wall portion 120 adjacent to the femoral artery 112 and vein 114, the femoral artery 112 and/or vein 114 may be inadvertently ruptured. Such a condition may become life threatening.

Some conventional endopylotomy devices and methods attempt to avoid cutting into the femoral artery 112 and/or femoral vein 114 by employing fluoroscopy to identify the location 104 of the femoral artery 112 and vein 114 and cutting at a location 122 opposite to the location 104. One disadvantage of this fluoroscopic approach is that it typically provides only two dimensional imaging. Another disadvantage is that appropriate fluoroscopy equipment is sometimes not readily available.

SUMMARY OF THE INVENTION

Accordingly, an object of the invention is to provide an improved device and methodology for performing an endopylotomy with reduced risk of inadvertently cutting into the femoral artery 112 and/or femoral vein 114 of a patient.

The invention generally relates to dilation catheters. More particularly, in one embodiment, the invention is directed to a catheter assembly having an elongated body, a dilatable bladder and a thermally responsive indicator. The elongated body has first and second ends and an outer wall. The dilatable bladder is incorporated with the elongated body and adapted to dilate in a radially outward direction from the elongated body. The thermally responsive indicator is incorporated with at least a portion of the dilatable bladder and adapted to exhibit a state in response to detecting a change in temperature.

According to a further embodiment, the elongated body defines a first internal lumen extending from the first end to the second end of the elongated body, and the dilatable bladder is adapted to inflate in response to a positive fluid pressure in the first lumen. According to another feature, the dilatable bladder deflates in response to a negative fluid pressure in the first lumen. In another embodiment, the dilatable bladder deflates in response to the positive fluid pressure being removed from the first lumen.

According to a further embodiment, the catheter assembly is adapted for insertion into a body of a mammal and the temperature change, and thus, the state change, is caused by a blood vessel being located proximally to the thermally responsive indicator. According to a further embodiment, the catheter assembly is adapted for insertion into a human ureter and the temperature change ,and thus, the state change, is caused by the thermally responsive indicator being located in close proximity to a blood vessel crossing the ureter at the utero-pelvic junction.

According to another embodiment, the catheter assembly is adapted to be deployed from a working lumen of an endoscope or like device. A fiber optic camera deployed in another lumen of the endoscope may be employed to observe any state changes In one embodiment, the dilatable bladder is substantially non-compliant. However, in other embodiments, the dilatable bladder is substantially compliant. In one embodiment, the dilatable bladder is formed separately from and then integrated with the elongated body. However, in other embodiments, a catheter body is treated to form a dilatable portion thereon. By way of example, in one embodiment, a portion of the elongated body is irradiated according to known methods to form the dilatable bladder.

According to one embodiment, the dilatable bladder radially circumscribes a longitudinal section of the elongated body. According to one feature of this embodiment, the dilatable bladder inflates radially outward from and circumscribes the longitudinal section of the elongated body in response to a positive fluid pressure from an inflation/deflation lumen in the elongated body. In an alternative embodiment, the dilatable bladder is disposed only around a portion of the section of the elongated body and thus, inflates radially outward from only the portion of the elongated body section.

In another alternative embodiment, the dilatable bladder includes at least two dilation chambers, which are independently dilatable via separate lumens in the elongated body. In one such embodiment, one chamber incorporates the thermally responsive detector and is employed to locate, for example, a crossing blood vessel. Whereas, the other chamber is used to deploy a surgical cutting wire located on its outer surface and adapted for incising a ureter.

According to one embodiment, the incorporated thermally responsive indicator is located on an outer surface of the dilatable bladder. In an alternative embodiment, the incorporated thermally responsive indicator is located on an inner surface of the dilatable bladder. In another alternative embodiment, the incorporated thermally responsive indicator includes a thermochromatic material and the thermochromatic material is dispersed in the material of the dilatable bladder. According to one embodiment, the thermochromatic material is incorporated over the entirety of the dilatable bladder. According to an alternative embodiment, the thermochromatic material is incorporated with only a portion of the dilatable bladder. In a further alternative embodiment, the thermochromatic material is incorporated at discrete locations of the dilatable bladder. As used with respect to the thermally responsive indicator "incorporated" includes, but is not limited to, coatings on an inner or outer surface or portion thereof of the dilatable bladder, dispersion within the material or a portion thereof of the dilatable bladder, and an independent material affixed over the dilatable bladder or a portion thereof.

In one preferred embodiment of the invention, the catheter assembly is adapted for insertion into a human ureter, and the thermally sensitive indicator changes state in response to the catheter assembly being positioned in the ureter at a location of a blood vessel crossing an external wall of the ureter. Such a crossing blood vessel sometimes occurs in at utero-pelvic junction. One use for detecting such a crossing vessel is to avoid damaging the crossing vessel during a ureteral surgical procedure, such as an endopylotomy.

According to one aspect of the invention, the catheter assembly includes a dedicated detector element adapted for detecting a thermally sensitive indicator state change and thus, the location of a crossing vessel. In one embodiment, the detector element is a fiber optic camera and the elongated body includes a detection lumen adapted for receiving the fiber optic camera to enable an operator to observe the state of the thermally sensitive indictor. In an embodiment wherein the thermally sensitive indicator is an thermochromatic material incorporated into a portion of the dilation element, using the fiber optic camera, an operator can observe a change in color of the portion of the dilation element in response to the dilation element encountering a crossing vessel.

In an alternative embodiment, the catheter assembly of the invention is deployed to a working channel of a conventional endoscope and rather than having a dedicated fiber optic camera, an operator views state changes through a non-dedicated fiber optic camera deployed through a viewing channel of the endoscope.

In a further embodiment, the catheter assembly of the invention includes a surgical cutting element. An operator uses the surgical cutting element to incise a portion of the ureter from within subsequent to establishing the position of any crossing blood vessel. In a typical endopylotomy procedure, the operator incises the ureter an inserts a stent to expand the inner diameter of the ureter to accommodate passage of, for example, kidney stones, or to relieve pressure caused, for example, by crossing blood vessels pushing against an outer wall of the ureter.

According to one feature, the surgical cutting element includes a wire located external to the elongated body and extends axially along the length of the dilation element. As the dilation element expands, the cutting wire extends radially outward to contact the inner wall of the ureter. When appropriately positioned, the operator can activate the cutting wire by, for example, passing a radio frequency current through the cutting wire. According to an alternative embodiment, the cutting wire extends axially along the length of the elongated body on an opposite side of the elongated body from the dilation element. In this embodiment, when the catheter assembly is appropriately positioned, the operator can manually extend the cutting wire radially outward from the elongated body to contact the inner wall of the ureter prior to activating the cutting current.

In another alternative embodiment, the elongated body includes a cutting lumen that extends from the first end of the elongated body to the second end of the elongated body and includes a cutting aperture extending radially through an inner wall of the cutting lumen and the external wall of the elongated body. According to one feature, the cutting aperture is located on an opposite side of the elongated body from the dilation element. According to one methodology, the operator repeatedly positions and inflates the dilation element until observing a state change. Upon observing the state change, the operator extends the cutting element along the cutting lumen and though the cutting aperture to incise the ureter at a diametrically opposite location from the location of the detected state change and thus, detected crossing blood vessel. In this embodiment, any conventional cutting element can be employed, including for example, a cold knife, a radio frequency cutter, and a laser cutter.

In one embodiment, one end of the cutting wire is anchored inside of the cutting lumen at a location between the cutting aperture and the second end of the elongated body, and extends axially from that location, past the cutting aperture toward the first end of the elongated body. The first end of the elongated body is adapted to enable the operator to extend the cutting wire into the cutting lumen to cause a looped section of the cutting wire to radially protrude from the cutting aperture and contact the inner wall of the ureter.

In an alternative embodiment, the cutting wire is not anchored inside of the cutting lumen. Instead, the cutting wire is shaped such that when the end of the cutting wire encounters the cutting aperture as the operator extends the cutting wire along the cutting lumen, the cutting wire tends to protrude axially from the cutting aperture to contact inner wall of the ureter.

According to a further embodiment of the invention, the operator flushes the dilatable bladder with a fluid of a particular temperature to initialize the state of the thermally responsive indicator. In one embodiment, the operator performs such flushing prior to inserting the catheter assembly. According to another embodiment, the operator performs such flushing subsequent to inserting the catheter assembly. In a further embodiment, the operator performs such flushing after each repositioning of the catheter assembly inside of the ureter.

The foregoing and other objects, aspects, features and advantages of the invention will become more apparent from the following description and from the claims.

BRIEF DESCRIPTION OF THE DRAWINGS

The foregoing and other objects of the invention and the various features thereof may be more fully understood from the following illustrative description when read together with the accompanying drawings in which like reference designations generally refer to the same parts throughout the different views and in which the depicted components are not necessarily drawn to scale.

ILLUSTRATIVE DESCRIPTION

As described above in summary, the invention is generally related to dilation catheters. More particularly, in one in illustrative embodiment, the invention provides a dilation catheter assembly adapted for performing an endopylotomy procedure. As mentioned above, during an endopylotomy, a medical operator risks inadvertently damaging a femoral artery or vein that crosses a patient's ureter (collectively-"crossing vessel"). According to the illustrative embodiment, the invention provides a mechanism for detecting the presence and location of such crossing vessels. Once located, the medical operator can choose an incision location that does not risk damage to the crossing vessel. As skilled artisans will appreciate, although the subject matter of the invention is discussed below with relation to the illustrative example of an endopylotomy and detecting a crossing vessel, the device and methods of the invention may be used to detect any feature that creates a thermal gradient between the feature and an internal temperature of an anatomical lumen.

Figures 2A, 2B:
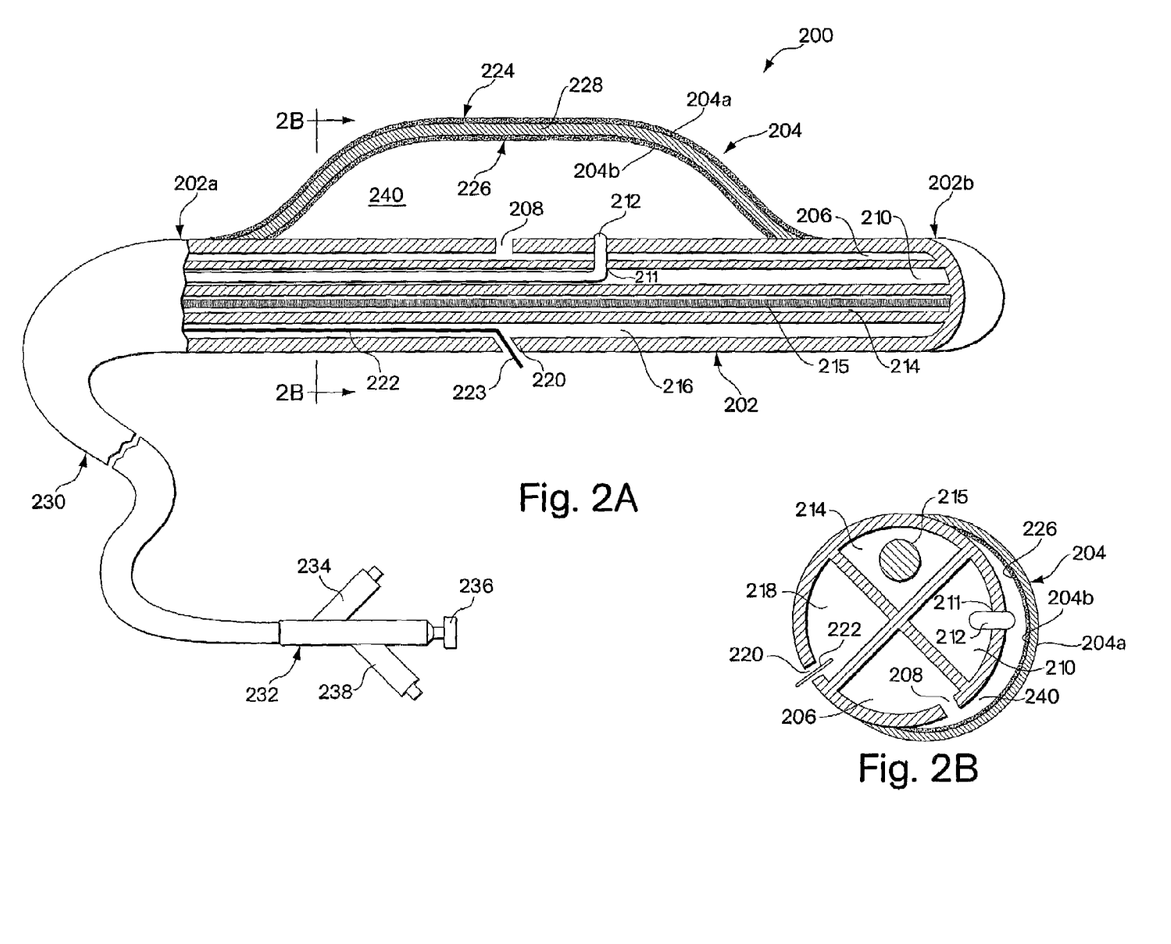
FIG. 2A is a longitudinal side view, partially in cross-section of dilatable catheter according to an illustrative embodiment of the invention.
FIG. 2B is a radial, cross-sectional view of the dilatable catheter of FIG. 2A taken along view 2B—2B.

FIG. 2A depicts a side view, partially in cross-section of a dilation catheter assembly 200 according to an illustrative embodiment of the invention. FIG. 2B shows a radial cross-sectional view of the catheter assembly 200 taken along view 2B—2B. Referring to FIGS 1A–2B, the dilation catheter assembly 200 is adapted for insertion into a body conduit, such as a human ureter. More particularly, the illustrative catheter assembly 200 is adapted for performing a surgical procedure from within a body conduit, such an endopylotomy from within a human ureter 104. As depicted, the catheter assembly 200 includes an elongated body 202 having first and second axially spaced ends 202a and 202b, respectively. The catheter assembly 200 also includes an dilatable bladder 204, an inflation/deflation conduit 206, a dedicated viewing conduit 210, a guide wire conduit 214 and a cutting element conduit 216.

In the illustrative embodiment, the dilatable bladder 204 is substantially non-compliant. However, in alternative embodiments, a compliant dilatable bladder 204 may be employed. A feature of the illustrative non-compliant, dilatable bladder 204 is that while it expands and contracts in a radial direction, substantially no expansion and contraction occurs in an axially direction. As shown in FIG. 2B, the illustrative dilatable bladder 216 extends around only a portion of the circumference of elongated body 202. The dilatable bladder 204 may be formed by any conventional approach, and may be formed either as an integral portion of or subsequently attached to the elongated body 202.

According to the illustrative embodiment, the dilatable bladder 204 incorporates a thermally responsive material, which changes states in response to being brought into proximity of the heat generated by the crossing vessels 112 and 114. According to a further illustrative embodiment, the thermally responsive material is a coating 224 of a thermochromatic material on an external surface 204a of the dilatable bladder 204. In an alternative illustrative embodiment, the thermally responsive material is a coating 226 of a thermochromatic material on an internal surface 204b of the dilatable bladder 204. In another alternative embodiment, the thermally responsive material is a thermochromatic material 228, incorporated into the material forming the dilatable bladder 204. One advantage of placing the thermochromatic material on the inner surface 204b is that it reduces any risk of the thermochromatic material leaching into a patients bloodstream. It should be noted that while FIG. 2A depicts all three possibilities for incorporating a thermally responsive material with the dilatable bladder 204, FIG. 2B only depicts the thermally responsive material disposed as a coating 226 on the inner surface 204b of the dilatable bladder 204. Although the illustrative embodiments of FIGS. 2A and 2B (and FIGS. 7A and 7B below) depict the thermally responsive material being disposed uniformly either on the outer surface 204a, inner surface 204a or throughout the material of the dilatable bladder 204, this need not be the case. Alternatively, the thermally responsive material may be coated or dispersed at only discrete portion(s) of the dilatable bladder 204.

As skilled artisans will appreciate, any conventional method for incorporating a thermochromatic material, such as a thermochromatic liquid crystalline polymer, onto the surfaces 204a or 204b or into the material forming the dilatable bladder 204 may be employed with the present invention. By way of example, variations of the approaches disclosed by U.S. Pat. No. 5,806,528 (Magliochetti), which describes a method for extruding a thermochromatic liquid crystalline polymer into a polymeric tube; U.S. Pat. No. Re 32,743 (Meyers et al.), which describes an elastic, flexible temperature responsive film for an inflatable temperature detector; U.S. Pat. No. 4,087,575 (Bichara), which describes stretchable, elastomeric films made from liquid crystal preparations; and/or U.S. Pat. No. 6,245,135 (Jaeger et al.), which describes a phase change ink, the disclosures of all of which are hereby incorporated by reference, may be employed to incorporate a thermally responsive material with the dilatable bladder 204, without departing from the scope of the invention.

The illustrative dilation catheter assembly 200 also includes a flexible extension 230. The flexible extension 230 terminates in an adapter 232. The adapter 232 includes an inflation/deflation valve 234, a cutting element connection/control interface 236 and a fiber optic viewing port 238.

The inflation/deflation conduit 206 extends from the second end 202b axially through the elongated section 202 and the flexible extension 230 and terminates at the inflation/deflation valve 234. The inflation/deflation conduit 206 includes a through aperture 208, adapted to provide fluid communication with the dilatable bladder 204. As described in further detail below with respect to FIGS. 5 and 6, according to the illustrative embodiment, upon insertion into a patient's body, prior to inflation for crossing vessel detection, a medical operator flushes the dilatable bladder 204 via the inflation/deflation valve 234 and the inflation/deflation conduit 206, with a relatively cold fluid to initialize the state of the thermally responsive material incorporated with the dilatable bladder 204.

The dedicated viewing conduit 210 extends axially from the second end 202b of the elongated body 202 through the flexible extension 230 and terminates at the fiber optic viewing port 238. The fiber optic viewing port 238 is adapted for connection to conventional viewing devices. As shown most clearly in FIG. 2B, the dedicated viewing conduit 210 includes an aperture 211 adapted for passing a conventional fiber optic viewing element 212 into an inner chamber 240 created by the dilatable bladder 204. Illustratively, the aperture 211 creates a fluid tight seal with the viewing element 212 so as not to effect inflation or deflation of the dilatable bladder 204.

The guide wire conduit 214 extends axially from the first end 202a of the elongated body 202 to the second end 202b of the elongated body 202 and is adapted to accommodate a conventional guide wire 215. The guide wire 215 is adapted for providing structural stiffness to the elongated body 202 during insertion into a patient. In alternative embodiments, the guide wire conduit may continue through the flexible extension 230 to a port on the adapter 232. In such an embodiment, the medical operator may insert and remove the guide wire 215 through the adapter 232 for increased operational flexibility.

The cutting element conduit 216 extends axially from the second end 202b of the elongated body 202 through the flexible extension 230 and terminates at the cutting element connection/control interface 236. The cutting element conduit 216 includes a cutting aperture 220, which varies in size depending on the type of cutting element being employed. As discussed in further detail below with respect to FIG. 5, the cutting aperture 220 is located substantially diametrically opposed to the portion of the dilatable bladder 204 that incorporates the thermally responsive material. According to the illustrative embodiment, any conventional surgical cutter adapted for operation though a catheter conduit may be employed, without departing from the scope of the invention. By way of example, without limitation, the illustrative embodiment may employ a cold knife, laser, or radio frequency cutting element. FIGS. 2A and 2B depict one embodiment of a radio frequency cutting element 222 formed from tungsten metal. In alternative embodiments, the radio frequency cutting element 222 may be formed from stainless steel.

The cutting element connection/control interface 236 is adapted to enable a medical operator to extend and retract the cutting end 223 of the cutting element 222. In the case of a laser cutting element 222, the interface 236 is further adapted to couple power to a laser cutting end 223. In the case of a radio frequency cutting element 222, the interface 236 is adapted to couple a radio frequency current to the cutting end 223.

Figure 3A:
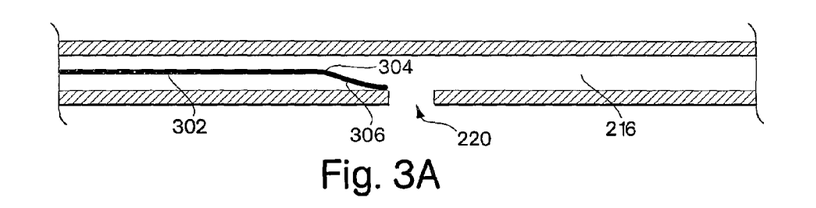
FIG. 3A is a longitudinal, cross-sectional view of a cutting element conduit of the dilatable catheter of FIG. 2A containing a surgical cutting element in a retracted position according to an illustrative embodiment of the invention.
Figure 3B:
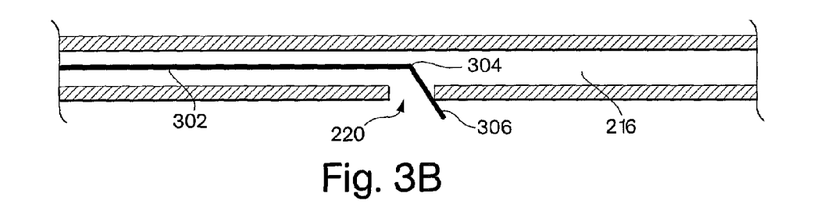
FIG. 3B is a longitudinal, cross-sectional view of a cutting element conduit of the dilatable catheter of FIG. 2A containing the surgical cutting element of FIG. 3A in a deployed position according to an illustrative embodiment of the invention.

FIGS. 3A depicts a longitudinal, cross-sectional view of a portion of a cutting element 302, according to one illustrative embodiment of the invention, in a retracted position within the cutting element conduit 216. FIG. 3B depicts a cross-sectional view of the cutting element 302 of FIG. 3A in a deployed position according to an illustrative embodiment of the invention. In the embodiments of FIGS. 3A and 3B, the cutting element 302 includes a bend or curve 304 at a cutting end 306. As shown in FIG. 3B, upon a medical operator extending the cutting element 302 through the cutting element conduit 216, the bent or curved cutting end 306 engages with and extends through the cutting aperture 220. Upon the medical operator retracting the cutting element 302, the cutting end 306 retracts back through the cutting aperture 220 and into the cutting element conduit 216. According to the illustrative embodiment, the cutting element 302 is either a radio frequency or cold knife surgical cutter.

Figure 4A:
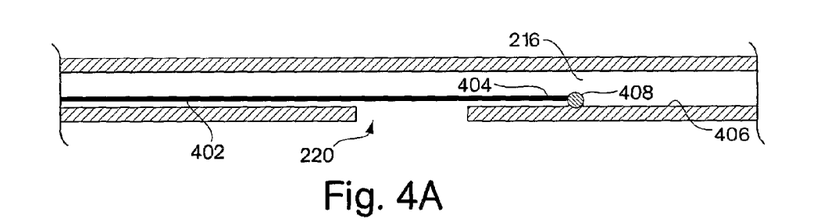
FIG. 4A is a longitudinal, cross-sectional view of a cutting element conduit of the dilatable catheter of FIG. 2A containing an alternative surgical cutting element in a retracted position according to an illustrative embodiment of the invention.
Figure 4B:
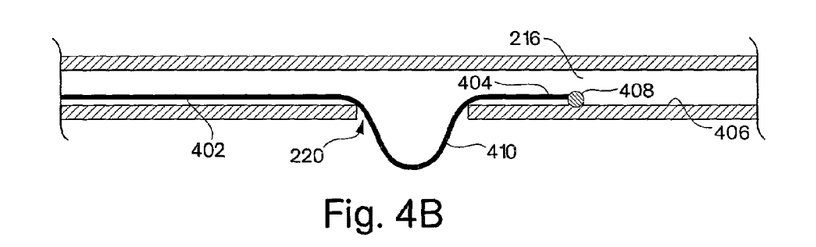
FIG. 4B is a longitudinal, cross-sectional view of a cutting element conduit of the dilatable catheter of FIG. 2A containing the surgical cutting element of FIG. 4A in a deployed position according to an illustrative embodiment of the invention.

FIG. 4A is a longitudinal, cross-sectional view of a portion of a cutting element 402, according to another illustrative embodiment of the invention, in a retracted position within the cutting element conduit 216. In the embodiment of FIG. 4A, a first end 404 anchors to an inner conduit wall 406 by way of a mount 408. As shown in FIG. 4B, in response to a medical operator extending the cutting element 402, a portion of the cutting element 402 bows out of the cutting aperture 220 to form a loop cutting portion 410. As in the embodiment of FIG. 4, the illustrative cutting element 402 is either a radio frequency or cold knife surgical cutter.

Figure 5:
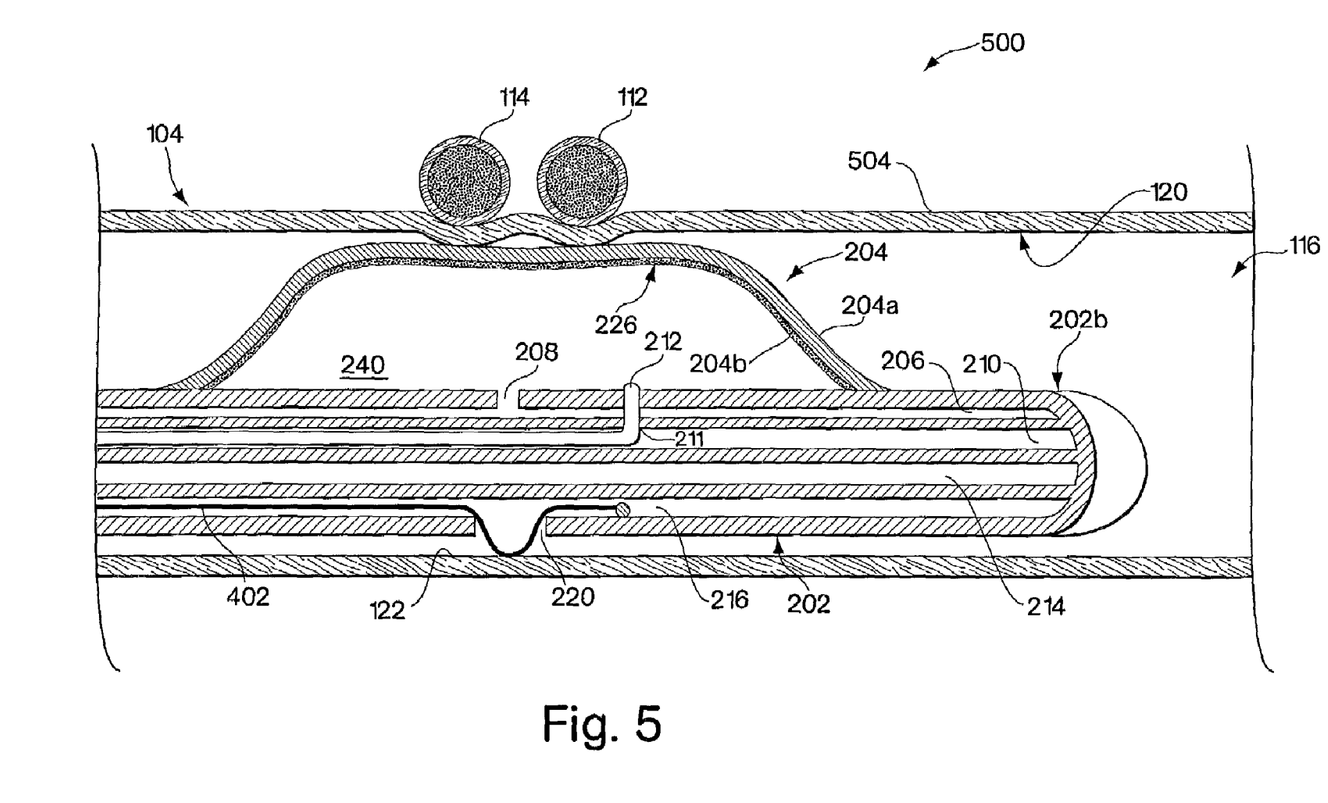
FIG. 5 is a longitudinal cross-sectional view of a portion of the dilatable catheter of FIG. 2A inserted into a patient's ureter according to an illustrative embodiment of the invention.

FIG. 5 depicts a longitudinal cross-sectional view 500 of a portion of the elongated body 202 of the dilation catheter assembly 200 of FIG. 2A inserted into a patient's ureter 104 according to an illustrative embodiment of the invention. As shown, in this illustrative example, the crossing vessels 112 and 114 are pressing on the ureter wall 104 causing flow to be impeded through the ureter lumen 116. According to the illustrative embodiment, subsequent to positioning the dilation catheter assembly 200 within the ureter lumen 116, the medical operator flushes the inner chamber 240 of the dilatable bladder 204, via the inflation/deflation lumen 206, with cooled saline solution to initialize the state of the thermochromatic coating 226 to an initial state (e.g., color). Next, the medical operator inflates the bladder 204, via the inflation/deflation lumen 206, to bring the outer wall 204a of the bladder 204 into contact with the inner wall portion 120. In response to heat generated from blood flow through the crossing vessels 112 and 114, the thermochromatic coating 226 changes state (e.g., changes color). The medical operator observes any such state change, for example, by way of the fiber optic camera 212, discussed above with respect to FIGS. 2A and 2B.

No state change or a reduced state change in the thermochromatic coating 226 indicates that the bladder 204 has been inflated in a portion of the ureter lumen 116 other than where the vessels 112 and 114 cross. Should that be the case, the medical examiner deflates the bladder 204, repositions the catheter assembly 200, re-inflates the bladder 204 and looks for the appropriate state change. Optionally, the medical examiner repeats the flushing of the inner chamber 240 with cooled saline solution or the like to reinitialize the state of the thermochromatic coating 226.

As mentioned above with respect to FIG. 2A, the cutting aperture 220 is located substantially diametrically opposite to the portion of the balloon that incorporates the thermochromatic coating 226. Thus, according to the illustrative embodiment, once the medial operator observes a state change indicating that the dilation catheter assembly 200 is positioned with the thermochromatic coating 226 proximate to the crossing vessels 112 and 114, it is safe to begin incising the inner wall portion 122 of the ureter 104, via the cutting aperture 220, without risking damage to the crossing vessels 112 and 114. As described above, the medical operator incises the wall portion 122 using any appropriate cutting device. In the illustrative embodiment of FIG. 5, the catheter assembly 200 employs a surgical cutting device 402 of the type described with respect to FIG. 4B. As skilled artisans will appreciate, subsequent to incising the wall portion 122 to widen the ureter lumen 116, a stent may be inserted until healing has occurred.

Figure 6:
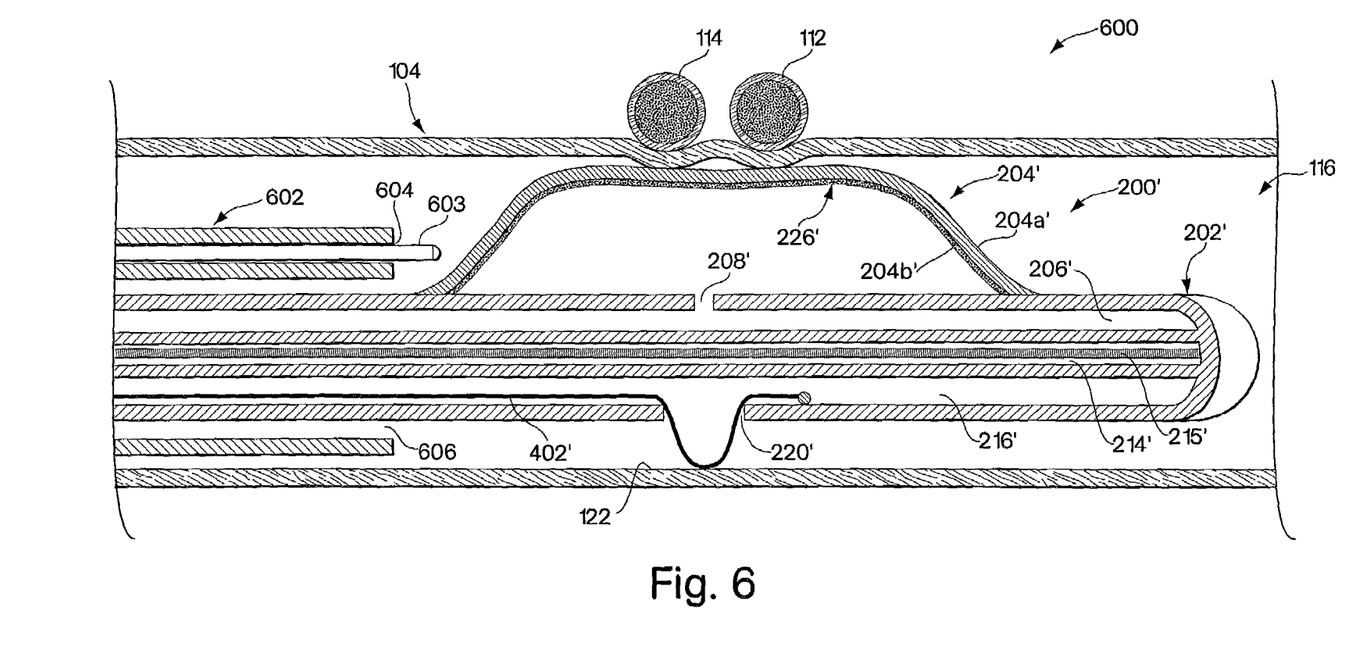
FIG. 6 is a longitudinal cross-sectional view of a portion of a dilatable catheter according to an alternative illustrative embodiment of the invention and inserted into a patient's ureter by way of an endoscope or similar device.

FIG. 6 depicts a longitudinal cross-sectional view 600 of a portion of an elongated body 202' of an alternative embodiment of the dilation catheter assembly 200 of FIG. 2A. In the illustrative embodiment of FIG. 6, the dilation catheter assembly 200' is deployed in a patient's ureter 104 through a working channel 606 of any conventional endoscope or like device 602. In FIG. 6, depicted elements having substantially equivalent counterparts in FIG. 2A are indicated by the use of primed reference designations. One difference between the dilation catheter assemblies 200 and 200' is that the dilation catheter assembly 200' does not need a dedicated optical conduit, such as the conduit 206. Instead, the inflatable/deflatable bladder 204' is formed to be translucent enough for a medical operator to view any state changes of the thermochromatic coating 226' by way of a conventional fiber optic camera 603 deployed through the lumen 604 of the endoscope 602. Alternatively, as described above with respect to FIG. 2A, the thermochromatic coating 226' may located on the external surface 204a' of the bladder 204', thus removing any need for the bladder 204' to be translucent. As in the embodiment of FIG. 5, upon locating the crossing vessels 112 and 114, the illustrative cutting element 402' enables the medical operator to safely incise the wall portion 122.

Figures 7A, 7B:
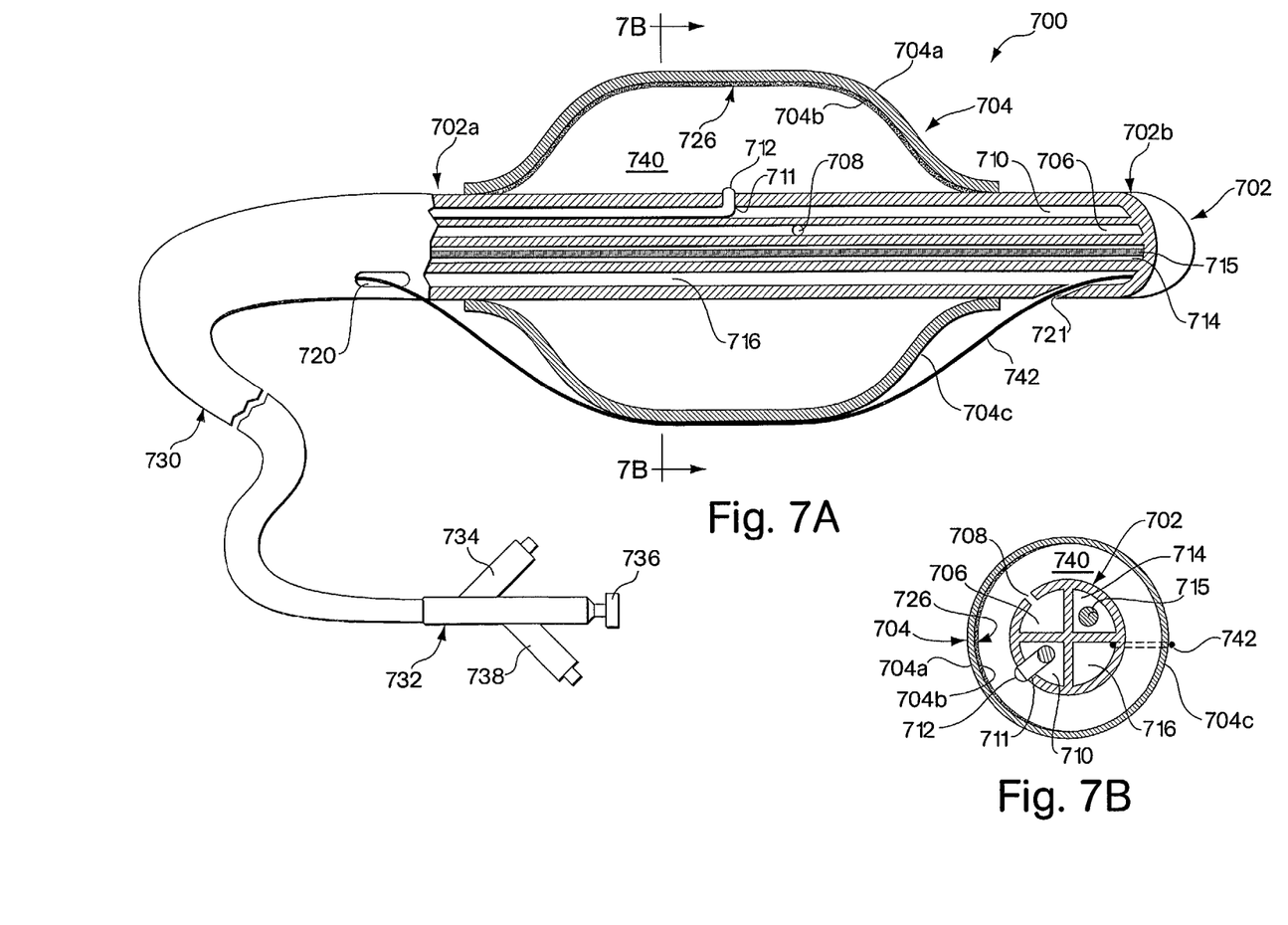
FIG. 7A is a longitudinal side view, partially in cross-section of dilatable catheter according to another alternative illustrative embodiment of the invention.
FIG. 7B is a radial, cross-sectional view of the dilatable catheter of FIG. 7A along view 7B—7B.

FIG. 7A is a side view, partially in cross-section of an alternative embodiment 700 of the dilation catheter assembly 200 of FIG. 2. FIG. 7B is a radial, cross-sectional view of the dilation catheter assembly 700 along the view 7B—7B. Referring to FIGS. 1A, 1B, 7A and 7B, the dilation catheter assembly 700 is also adapted for performing a surgical procedure from within a body conduit, such an endopylotomy from within a human ureter 104. As depicted, the catheter assembly 700 includes an elongated body 202 having first and second axially spaced ends 702a and 702b, respectively. The catheter assembly 700 also includes an dilatable bladder 704, an inflation/deflation conduit 706, a dedicated viewing conduit 710, a guide wire conduit 714 and a cutting element conduit 716.

In the illustrative embodiment, the dilatable bladder 704 is substantially non-compliant. However, in alternative embodiments, a compliant dilatable bladder 704 may be employed. A feature of the illustrative non-compliant, dilatable bladder 704 is that while it expands and contracts in a radial direction, substantially no expansion and contraction occurs in an axially direction. As shown in FIG. 7B, unlike the catheter assembly 200 of FIGS. 2A and 2B, the dilatable bladder 704 extends around the entire circumference of at least a portion of the elongated body 702. The dilatable bladder 704 may be formed by any conventional approach, and may be formed either as an integral portion of or subsequently integrated with the elongated body 702.

As in the case of the dilatable bladder 204, the dilatable bladder 704 incorporates a thermally responsive material, which changes states in response to being brought into proximity of the heat generated by the crossing vessels 112 and 114. The illustrative thermally responsive material is depicted as a thermochromatic coating 726 on an internal surface 704b of the dilatable bladder 704. However, as described above with respect to FIGS. 2A and 2B, in alternative illustrative embodiments, the thermally responsive material may be, for example, coated onto discrete locations of the inner surface 704b, discrete locations of or the entire external surface 704a or may be incorporated into the material forming the dilatable bladder 704, uniformly or at discrete locations.

The illustrative dilation catheter assembly 700 also includes a flexible extension 730. The flexible extension 730 terminates in an adapter 732. The adapter 732 includes an inflation/deflation valve 734, a cutting element connection/control interface 736 and a fiber optic viewing port 738.

The inflation/deflation conduit 706 extends from the second end 702b axially through the elongated section 702 and the flexible extension 730 and terminates at the inflation/deflation valve 734. The inflation/deflation conduit 706 includes a through aperture 708, adapted to provide fluid communication with the dilatable bladder 704. As described in further detail below with respect to FIGS. 10 and 11, according to the illustrative embodiment, upon insertion into a patient's body, prior to inflation for crossing vessel detection, a medical operator flushes the dilatable bladder 704 via the inflation/deflation valve 734 and the inflation/deflation conduit 706, with a relatively cold fluid to initialize the state of the thermally responsive material incorporated with the dilatable bladder 704.

The dedicated viewing conduit 710 extends axially from the second end 702b of the elongated body 702 through the flexible extension 730 and terminates at the fiber optic viewing port 738. The fiber optic viewing port 738 is adapted for connection to conventional viewing devices. As shown in FIGS. 7A and 7B, the dedicated viewing conduit 710 includes an aperture 711 adapted for passing a conventional fiber optic viewing element 712 into an inner chamber 740 created by the dilatable bladder 704. Illustratively, the aperture 711 creates a fluid tight seal with the viewing element 712 so as not to effect inflation or deflation of the dilatable bladder 704.

The guide wire conduit 714 extends axially from the first end 702a of the elongated body 702 to the second end 702b of the elongated body 702 and is adapted to accommodate a conventional guide wire 715. The guide wire 715 is adapted for providing structural stiffness to the elongated body 702 during insertion into a patient. In alternative embodiments, the guide wire conduit 714 may continue through the flexible extension 730 to a port on the adapter 732. In such an embodiment, the medical operator may insert and remove the guide wire 715 through the adapter 732 for selectively providing increased operational stiffness to the catheter assembly 700.

The cutting element conduit 716 extends axially from the second end 702b of the elongated body 702 through the flexible extension 730 and terminates at the cutting element connection/control interface 736. The cutting element conduit 716 includes cutting apertures 720 and 721, which vary in size depending on the type of cutting element being employed. The cutting element 742 extends through the cutting element conduit 716 from the second end 702b of the elongated body 702, out of the cutting aperture 721, along an external surface portion 704c of the dilatable bladder 704, back into the cutting element conduit 716 by way of the cutting aperture 720, and through the flexible extension 730 to the cutting element connection/control interface 736. According to the illustrative embodiment of FIGS. 7A and 7B, any conventional surgical cutter adapted for operation though a catheter conduit may be employed, without departing from the scope of the invention.

As shown in FIG. 7A, and as discussed in further detail below with respect to FIGS. 8 and 9, to reduce the risk of damaging the crossing vessels 112 and 114, the external surface portion 704c along which the cutting element 716 extends is substantially diametrically opposed from the inner and outer surface portions 704a and 704b where the thermally responsive material is disposed. However, according to alternative embodiments, the thermally responsive material may be throughout the dilatable bladder 704, with the location of the state change being detected by a fiber optic camera such as the camera 712, discussed if further detail below.

According to one feature, the dilatable bladder 704 is inflated enough to bring the thermochromatic coating 726 into sufficient proximity with the inside wall portion 120 to cause a state change in response to detecting the femoral artery 112 or vein 114, but not close enough to cause the cutting element 742 to incise adjacent tissue. Subsequent to locating the femoral artery 112 and vein 114 through one or more of inflation/deflation cycles described above with respect to FIG. 2A, the medical operator can then inflate the dilatable bladder 704 sufficiently to enable the cutting element 742 to incise the inner wall portion 122.

According to another feature, the cutting element connection/control interface 736 is adapted to enable the cutting element 742 to extend automatically in response to the dilatable bladder 704 expanding. According to a further feature, the connection/control interface 736 is adapted to enable a medical operator to retract the cutting element 742 as the dilatable bladder 704 contracts. According to an additional feature, the interface 736 is adapted to enable the medical operator to extend the cutting element 742 as the dilatable bladder 704 expands and/or to extend the cutting element 742 an additional amount after the dilatable bladder 704 is fully expanded. In the case of a powered cutting element 742, the connection/control interface 736 is adapted to couple such power to the cutting element 742.

Figure 8:
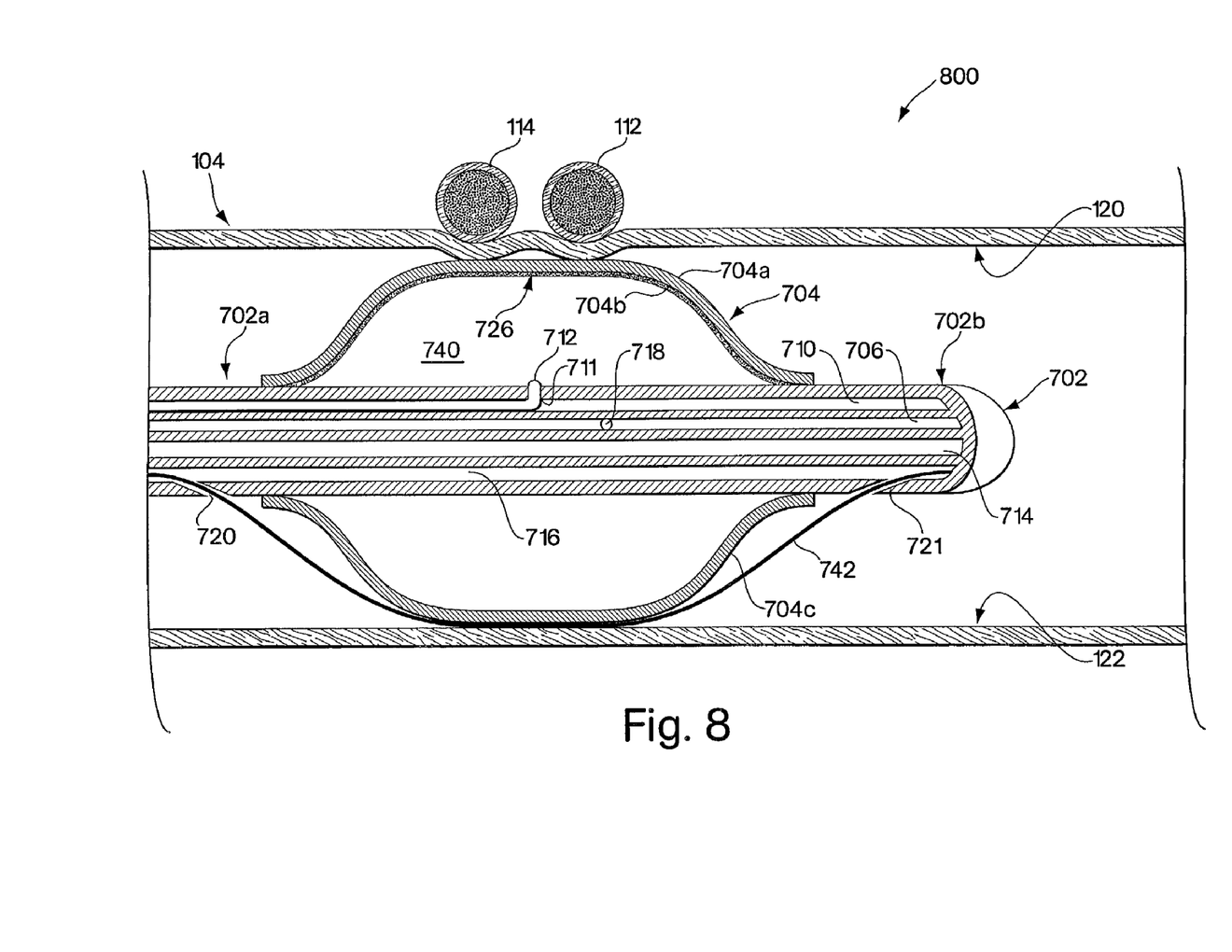
FIG. 8 is a longitudinal, cross-sectional view of a portion of the dilatable catheter of FIG. 7A inserted into a patient's ureter according to an illustrative embodiment of the invention.

FIG. 8 depicts a longitudinal cross-sectional view 800 of a portion of the elongated body 702 of the dilation catheter assembly 700 of FIG. 7A inserted into a patient's ureter 104 according to an illustrative embodiment of the invention. As in the case FIG. 5, the crossing vessels 112 and 114 are pressing on the ureter wall 104 causing flow to be impeded through the ureter lumen 116. According to the illustrative embodiment, subsequent to positioning the dilation catheter assembly 700 within the ureter lumen 116, the medical operator flushes the inner chamber 740 of the dilatable bladder 704, via the inflation/deflation lumen 706, with cooled saline solution to initialize the state of the thermochromatic coating 726 to an initial state (e.g., color). Next, the medical operator inflates the bladder 704, via the inflation/deflation lumen 706, to bring the outer wall 704a of the bladder 704 into proximity with the inner wall portion 120, but not close enough to cause the cutting element 742 to incise adjacent tissue. In response to heat generated from blood flow through the crossing vessels 112 and 114, the thermochromatic coating 726 changes state (e.g., changes color). The medical operator observes any such state change, for example, by way of the fiber optic camera 712, discussed above with respect to FIGS. 7A and 7B.

No state change or a reduced state change in the thermochromatic coating 726 indicates that the bladder 704 has been inflated in a portion of the ureter lumen 116 other than where the crossing vessels 112 and 114 contact the ureter 104. Should that be the case, the medical examiner deflates the bladder 704, repositions the catheter assembly 700, re-inflates the bladder 704 and looks for the appropriate state change. Optionally, the medical examiner repeats the flushing of the inner chamber 740 with cooled saline solution or the like to reinitialize the state of the thermochromatic coating 726.

As mentioned above with respect to FIG. 7A, the cutting element 742 is located substantially diametrically opposite to the portion of the balloon that the camera 712 is viewing for a state change. Thus, according to the illustrative embodiment, once the medial operator observes the state change, indicating that the dilation catheter assembly 700 is positioned with the thermochromatic coating 726 proximate to the crossing vessels 112 and 114, it is safe to begin incising the inner wall portion 122 of the ureter 104, via the cutting element 742, without risking damage to the crossing vessels 112 and 114. As described above with respect to FIG. 7A, the medical operator incises the wall portion 122 by extending the cutter element 742 either by further inflation of the bladder 704 or by way of the cutting element connection/control interface 736.

Figure 9:
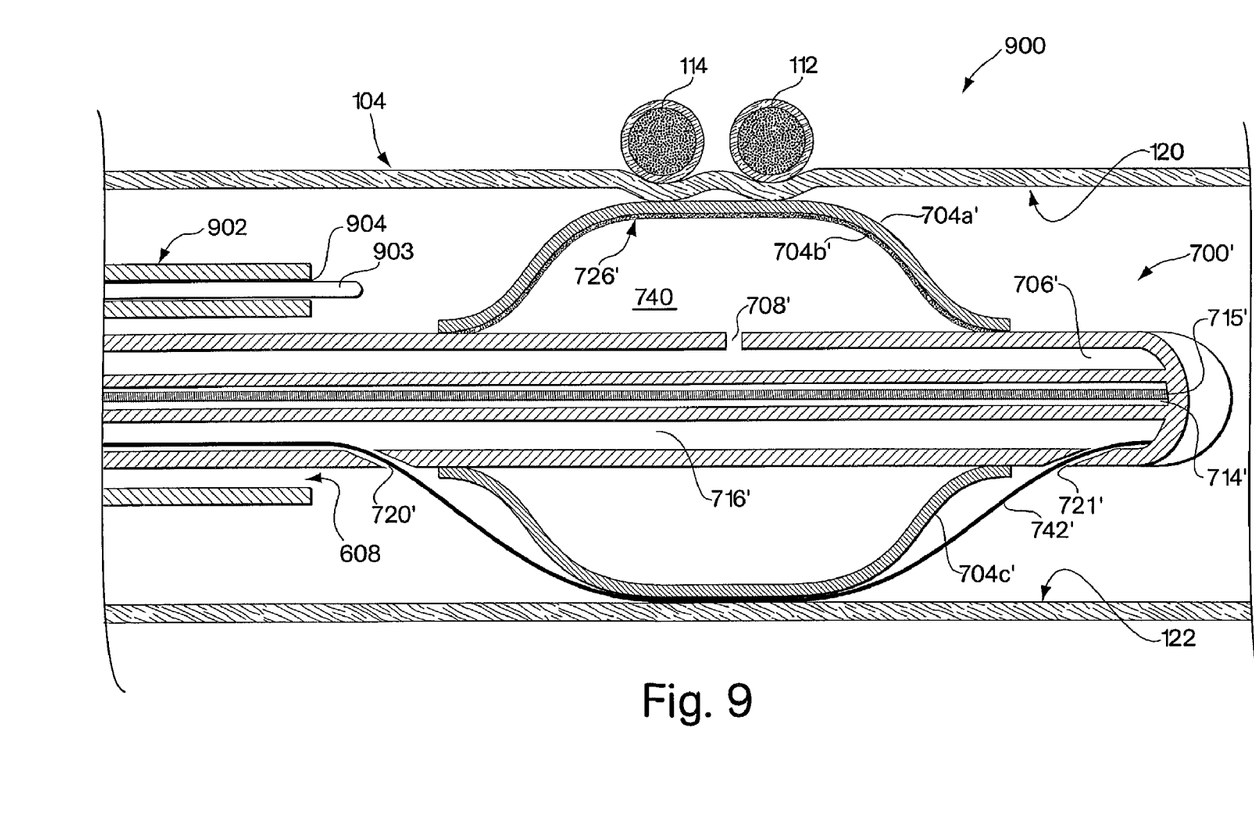
FIG. 9 is a longitudinal, cross-sectional view of a portion of a dilatable catheter according to another alternative illustrative embodiment of the invention and inserted into a patient's ureter by way of an endoscope or similar device.

FIG. 9 depicts a longitudinal cross-sectional view 900 of a portion of an elongated body 702' of an alternative embodiment of the dilation catheter assembly 700 of FIG. 7A. In the illustrative embodiment of FIG. 9, the dilation catheter assembly 900' is deployed in a patient's ureter 104 through a working channel 906 of any conventional endoscope or like device 602. In FIG. 9, depicted elements having substantially equivalent counterparts in FIG. 7A are indicated by the use of primed reference designations. One difference between the dilation catheter assemblies 700 and 700' is that the dilation catheter assembly 700' does not need a dedicated optical conduit, such as the conduit 706. Instead, the inflatable/deflatable bladder 704' is formed to be translucent enough for a medical operator to view any state changes of the thermochromatic coating 726' by way of a conventional fiber optic camera 903 deployed through the lumen 904 of the endoscope 902. Alternatively, as described above with respect to FIG. 7A, the thermochromatic coating 726' may located on the external surface 704a' of the bladder 704', thus removing any need for the bladder 704' to be translucent. As in the embodiment of FIG. 8, upon locating the crossing vessels 112 and 114, the illustrative cutting element 742' enables the medical operator to safely incise the wall portion 122.

The invention may be embodied in other specific forms without departing from the spirit or essential characteristics thereof. Accordingly, the above described embodiments are to be considered in all respects as illustrative and not restrictive, the scope of the invention being indicated by the appended claims, rather than by the foregoing description, and all changes which come within the meaning and range of equivalency of the claims are intended to be embraced therein.

What is claimed is:

1. A catheter assembly comprising,
    an elongated body having a first end portion and a second end portion,
    a dilatable bladder incorporated with said elongated body between the first end portion of the elongated body and the second end portion of the elongated body, the dilatable bladder being adapted to dilate in a radially outward direction from said elongated body, a thermally responsive indicator incorporated with at least a portion of said dilatable bladder, said thermally responsive indicator being adapted to visually change in response to a change in temperature, and a surgical cutter adapted to enable an operator to cut mammal flesh at a location other than the location of said thermally responsive indicator.

2. The catheter assembly of claim 1, wherein said elongated body defines an internal lumen extending from a first end of said elongated body to a second end of said elongated body, said dilatable bladder is in fluid communication with said internal lumen, and inflates in response to a positive fluid pressure in said internal lumen.

3. The catheter of claim 1, wherein said catheter is adapted for insertion into a body of a mammal and said thermally responsive indicator detects a change in temperature when said thermally responsive indicator is located in proximity of a blood vessel.

4. The catheter of claim 1, wherein said catheter is adapted for insertion into a human body and said thermally responsive indicator indicates a change in temperature when a portion of said dilatable bladder is disposed in a ureter and brought into proximity of a femoral artery or vein.

5. The catheter assembly of claim 1, wherein said dilatable bladder has an inner surface and said thermally responsive indicator is disposed on at least a portion of said inner surface.

6. The catheter assembly of claim 1, wherein said dilatable bladder has an outer surface and said thermally responsive indicator is disposed on at least a portion of said outer surface.

7. The catheter assembly of claim 1, wherein said thermally responsive indicator includes a thermochromatic material.

8. The catheter assembly of claim 7, wherein said dilatable bladder is formed from a first material and said thermochromatic material is disposed within said first material.

9. The catheter assembly of claim 1, further comprising a detector element adapted for detecting the visual change of said thermally responsive indicator.

10. The catheter assembly of claim 9, wherein said elongated body defines a detector lumen extending between the first end portion of said elongated body and the second end portion of said elongated body, and being adapted for receiving said detector element.

11. The catheter assembly of claim 9, wherein said detector element is a fiber optic camera adapted to enable an operator to view the visual change of said thermally responsive indicator.

12. The catheter assembly of claim 1, wherein said dilatable bladder extends around a first portion of a periphery of said elongated body and said surgical cutter is adapted to enable an operator to cut mammal flesh contacting a second portion of the periphery of said elongated body, said first portion of the periphery of said elongated body and said second portion of the periphery of said elongated body being non-overlapping.

13. The catheter assembly of claim 1, wherein said thermally responsive indicator is adapted to change color in response to a change in temperature.

14. The catheter assembly of claim 1, wherein said thermally responsive indicator is adapted to visually change in response to a change in temperature from a source external of said bladder.

15. The catheter assembly of claim 1, wherein said thermally responsive indicator is adapted to visually change in response to a change in temperature from a first temperature present in a ureter adjacent at least one of a femoral artery and vein of a patient to a second temperature present in the ureter spaced from the femoral artery and vein of the patient.

16. The catheter assembly of claim 1, wherein the elongated body includes a first portion and a second portion different than the first portion of the elongated body, and the bladder is entirely incorporated with the first portion of the elongated body.

17. The catheter assembly of claim 1, wherein
the elongated body includes a first portion and a second portion different than the first portion of the elongated body, the bladder is entirely incorporated with the first portion of the elongated body, the cutter is disposed on the second portion of the elongated body.

18. A catheter assembly comprising,
an elongated body having a first end portion and a second end portion,
a dilatable bladder incorporated with said elongated body between the first end portion of the elongated body and the second end portion of the elongated body, the dilatable bladder being adapted to dilate in a radially outward direction from said elongated body,
a thermally responsive indicator incorporated with at least a portion of said dilatable bladder, said thermally responsive indicator being adapted to visually change in response to a change in temperature,
a cutting lumen extending from the first end portion of said elongated body to the second end portion of said elongated body, wherein an outer wall of said elongated body includes a cutting aperture in communication with said cutting lumen, and
a surgical cutting wire anchored in said cutting lumen at a location between said cutting aperture and said second end portion of said elongated body, and extending axially from said location past said cutting aperture toward said first end portion of said elongated body, wherein said cutting lumen at said first end portion of said elongated body is adapted to enable an operator to extend said surgical cutting wire to cause a looped portion of said surgical cutting wire to protrude radially through said cutting aperture.

19. A catheter assembly comprising,
an elongated body having a first end portion and a second end portion,
a dilatable bladder incorporated with said elongated body between the first end portion of the elongated body and the second end portion of the elongated body, the dilatable bladder being adapted to dilate in a radially outward direction from said elongated body,
a thermally responsive indicator incorporated with at least a portion of said dilatable bladder, said thermally responsive indicator being adapted to visually change in response to a change in temperature,
a cutting lumen extending from the first end portion of said elongated body to the second end portion of said elongated body, wherein an outer wall includes a cutting aperture in communication with said cutting lumen, and
a surgical cutting element adapted to extend axially from said first end portion through said cutting lumen toward said cutting aperture, wherein said cutting lumen at said first end portion of said elongated body is adapted to enable an operator to extend and retract said surgical cutting element radially through said cutting aperture.

20. A catheter assembly comprising,
an elongated body having a first end portion and a second end portion,
a dilatable bladder incorporated with said elongated body between the first end portion of the elongated body and the second end portion of the elongated body, the dilatable bladder being adapted to dilate in a radially outward direction from said elongated body,
a thermally responsive indicator incorporated with at least a portion of said dilatable bladder, said thermally responsive indicator being adapted to visually change in response to a change in temperature, and
a surgical cutting wire extending external to said elongated body from a first location proximal to a first end of said elongated body to a second location proximal to a second end of said elongated body, said surgical cutting wire disposed in a fixed relationship to said second location and in a moveable relationship with said first location, said first location being adapted to enable an operator to extend and retract said surgical cutting element to adjust an amount of radial protrusion of said cutting element from said elongated body.

21. A catheter assembly comprising,
an elongated body having a first end portion and a second end portion,
a dilatable bladder incorporated with said elongated body between the first end portion of the elongated body and the second end portion of the elongated body, the dilatable bladder being adapted to dilate in a radially outward direction from said elongated body, the dilatable bladder having an outer surface, and
a thermally responsive indicator incorporated with at least a portion of said dilatable bladder, said thermally responsive indicator being adapted to visually change in response to a change in temperature, and
a surgical cutting wire extending adjacent to said outer surface of said dilatable bladder from a first location proximal to the first end portion of said elongated body to a second location proximal to the second end portion of said elongated body, said surgical cutting wire disposed in a fixed relationship to said second location and in a moveable relationship to said first location.

22. The catheter assembly of claim 21, wherein said surgical cutting wire is adapted to extend in response to inflation of said dilatable bladder and retract in response to deflation of said dilatable bladder.

23. A catheter assembly, comprising,
an elongated body having a first end portion and a second end portion,
a dilatable bladder coupled to said elongated body between the first end portion of the elongated body and the second end portion of the elongated body, the dilatable bladder being adapted to dilate in a radially outward direction from said elongated body,
a thermally responsive indicator, at least a portion of said thermally responsive indicator being disposed on at least a portion of said dilatable bladder, said at least a portion of said thermally responsive indicator being adapted to visually change in response to a change in temperature, and
a detector element adapted for detecting the visual change of said at least a portion of said thermally responsive indicator.

24. The catheter assembly of claim 23, wherein said elongated body defines an internal lumen extending from the first end portion of said elongated body to the second end portion of said elongated body, said dilatable bladder is in fluid communication with said internal lumen, and inflates in response to a positive fluid pressure in said internal lumen.

25. The catheter assembly of claim 23, wherein said catheter is adapted for insertion into a body of a mammal and said at least a portion of said thermally responsive indicator indicates a change in temperature when said at least a portion of said thermally responsive indicator is brought into proximity of a blood vessel.

26. The catheter assembly of claim 23, wherein said catheter is adapted for insertion into a human body and said at least a portion of said thermally responsive indicator indicates a change in temperature when a portion of said dilatable bladder is disposed in a ureter and is brought into proximity of a femoral artery or vein.

27. The catheter assembly of claim 23, wherein a portion of said elongated body is adapted to form said dilatable bladder.

28. The catheter assembly of claim 23, wherein said dilatable bladder has an inner surface and said at least a portion of said thermally responsive indicator is disposed on at least a portion of said inner surface.

29. The catheter assembly of claim 23, wherein said dilatable bladder has an outer surface and said at least a portion of said thermally responsive indicator is disposed on at least a portion of said outer surface.

30. The catheter assembly of claim 23, wherein said thermally responsive indicator includes a thermochromatic material.

31. The catheter assembly of claim 23, wherein said dilatable bladder is formed from a first material and said thermochromatic material is disposed within said first material.

32. The catheter assembly of claim 23, further comprising, a detector lumen extending between the first end portion of said elongated body and the second end portion of said elongated body, and being adapted for receiving said detector element.

33. The catheter assembly of claim 23, wherein said detector element is a fiber optic camera adapted to enable an operator to view the visual change of said at least a portion of said thermally responsive indicator.

34. The catheter assembly of claim 23, further comprising,
a surgical cutter adapted to enable an operator to cut mammal flesh at a location other than a location of said at least a portion of said thermally responsive indicator when said at least a portion of said thermally responsive indicator indicates a change in temperature.

35. The catheter assembly of claim 23, wherein said dilatable bladder extends around a first portion of a periphery of said elongated body and said catheter assembly further comprises a surgical cutter adapted to enable an operator to incise mammal flesh contacting a second portion of the periphery of said elongated body, said first portion of the periphery of said elongated body and said second portion of the periphery of said elongated body being non-overlapping.

36. The catheter assembly of claim 23, further comprising,
a cutting lumen extending from the first end portion of said elongated body to the second end portion of said elongated body, wherein an outer wall of said elongated body includes a cutting aperture in communication with said cutting lumen, and a surgical cutting wire anchored in said cutting lumen at a location between said cutting aperture and said second end portion of said elongated body, and extending axially from said location past said cutting aperture toward said first end portion of said elongated body, wherein said cutting lumen at said first end of said elongated body is adapted to enable an operator to extend said surgical cutting wire to cause a looped portion of said surgical cutting wire to protrude radially through said cutting aperture.

37. The catheter assembly of claim 23, further comprising, a cutting lumen extending from the first end portion of said elongated body to the second end portion of said elongated body, wherein an outer wall includes a cutting aperture in communication with said cutting lumen, and a surgical cutting element adapted to extend axially from said first end portion through said cutting lumen toward said cutting aperture, wherein said cutting lumen at said first end portion of said elongated body is adapted to enable an operator to extend and retract said surgical cutting element radially through said cutting aperture.

38. The catheter assembly of claim 23, further comprising, a surgical cutting wire extending external to said elongated body from a first location proximal to the first end portion of said elongated body to a second location proximal to the second end portion of said elongated body, said surgical cutting wire disposed in a fixed relationship to said second location and in a moveable relationship with said first location, said first location being adapted to enable an operator to extend and retract said surgical cutting element to adjust an amount of radial protrusion of said cutting element from said elongated body.

39. The catheter assembly of claim 23, wherein said dilatable bladder has an outer surface and said catheter assembly further comprises, a surgical cutting wire extending adjacent to said outer surface of said dilatable bladder from a first location proximal to the first end portion of said elongated body to a second location proximal to the second end portion of said elongated body, said surgical cutting wire disposed in a fixed relationship to said second location and in a moveable relationship to said first location.

40. The catheter assembly of claim 39, wherein said surgical cutting wire is adapted to extend in response to inflation of said dilatable bladder and retract in response to deflation of said dilatable bladder.

41. The catheter assembly of claim 23, wherein said at least a portion of said thermally responsive indicator is adapted to change color in response to a change in temperature.

* * * * *